(12) United States Patent
Ritter et al.

(10) Patent No.: US 6,437,065 B1
(45) Date of Patent: *Aug. 20, 2002

(54) REACTIVE SYSTEMS FROM POLYMERIZABLE MONOMERS WHICH COMPRISE PEROXIDES AND STABILIZED ALKYLBORON COMPOUNDS

(75) Inventors: Wolfgang Ritter, Haan; Robert Wenz, Wöllstadt; Peter Pokinskyj, Rossdorf, all of (DE)

(73) Assignee: Merck Patent Gesellschaft mit beschrankter Haftung (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/392,507

(22) Filed: Sep. 10, 1999

(30) Foreign Application Priority Data

Sep. 10, 1998 (DE) .......................................... 198 41 342

(51) Int. Cl.[7] .................................................. C08F 4/28
(52) U.S. Cl. ..................... 526/227; 526/124.6; 526/134; 526/196; 526/317; 526/328.5; 524/183; 524/522; 524/523; 524/556; 524/560
(58) Field of Search ................................ 524/522, 523, 524/556, 560; 526/134, 196, 317, 328, 328.5

(56) References Cited

U.S. PATENT DOCUMENTS

| | | | | | |
|---|---|---|---|---|---|
| 4,381,386 A | * | 4/1983 | Ritter et al. | ................ | 526/239 |
| 4,385,153 A | * | 5/1983 | Ritter | ......................... | 524/522 |
| 4,676,858 A | * | 6/1987 | Ritter | ......................... | 156/307 |
| 5,461,124 A | * | 10/1995 | Ritter et al. | .................. | 526/84 |
| 5,482,717 A | * | 1/1996 | Fues et al. | ................... | 424/426 |
| 5,552,454 A | * | 9/1996 | Kretschmann et al. | ...... | 523/113 |
| 5,648,518 A | * | 7/1997 | Ritter et al. | ................ | 560/224 |

* cited by examiner

*Primary Examiner*—David W. Wu
*Assistant Examiner*—Tatyana Zalukaeva
(74) *Attorney, Agent, or Firm*—Millen, White, Zelano & Branigan, P.C.

(57) ABSTRACT

Reactive systems for polymerizing ethylenically unsaturated compounds comprising a first component, comprised of ethylenically unsaturated compounds capable of polymerization, and a second component of a hardener system comprised of organoboron compounds which are stabilized with suitable oligomers. An organic peroxide (perester, hydroperoxide, perether and/or peranhydride) is admixed with the compounds. These components are mixed to form a polymer. The reactive system reaches full strength in reduced time with the use of the organic peroxide and are suitable for joining hard body materials in human or animal tissue, in particular in the surgical and/or dental sector, in the production of body-absorbable or body-resistant adhesives, cements, and/or filling compounds and for forming synthetic material moldings.

21 Claims, No Drawings

REACTIVE SYSTEMS FROM POLYMERIZABLE MONOMERS WHICH COMPRISE PEROXIDES AND STABILIZED ALKYLBORON COMPOUNDS

The present invention describes reactive systems which are composed of ethylenically unsaturated monomers on the one hand, and of oxygen-reactive organoboron compounds which are stabilized by means of carrier materials on the other hand. The monomer component additionally comprises small amounts of peroxides.

The novel reactive systems are suitable in principle for many applications, for example for the industrial or craft sector, but they have a particular and is preferred significance for use in medicine in human or animal tissue. They are suitable as binders or adhesives for bonding endogenous hard tissue and for bonding such tissue to synthetic material and/or metal and/or for in situ formation of synthetic material moldings in surgical work. They are used in particular in the area of reactive adhesive and cement systems for medical and/or dental applications and, in the last-mentioned area, also as filling materials.

Polymer-based synthetic materials, and reactive systems curable by initiation of reaction are becoming increasingly important both in human medicine and in the veterinary sector. Reference may be made to surgical and/or dental adhesives, cements, filling materials and the like which usually set after application and implantation into the living body and then remain in contact with the living body. The curable adhesives preferably employed in practice normally consist of the following components:

one or more free-radical polymerizable, ethylenically unsaturated monomers which are, where appropriate, mixed with inhibitors to prevent unwanted premature initiation of reaction;

a starter system to initiate polymerization;

polymers for improving cohesion and adjusting the viscosity and, where appropriate, active fillers for improving the mechanical properties.

A starter system frequently used to initiate polymerization in reaction systems comprising ethylenic double bonds consists of oxygen-reactive organoboron compounds. There is a wide-ranging literature on this, and therefore the following publications may be cited as only a small selection: DE 30 41 843, DE 30 41 904, DE 31 43 945, DE 32 01 780, DE 32 04 504 or else DE 32 29 635.

DE 39 39 164 likewise describes starter systems based on oxygen-active organoboron compounds which are combined with a carrier material. The carriers employed are oligoesters of lower hydroxy carboxylic acids. These carriers improve the stability of the system towards oxygen. In order for such reactive boron compounds such as, for example, 9-borabicyclo[3.3.1]nonane (9-BBN) in fact to be processible and stable on storage, they are introduced into a matrix of an ester of a polyhydric alcohol, and of an oligomer of a hydroxy carboxylic acid.

However, even these systems are not optimal because it has been found that the storage stability is inversely proportional to the concentration of the boron compound. It would therefore be desirable to have starter systems or reactive systems in which the concentration of organoboron compounds was as low as possible, also because of the toxicity of the boron compounds, but without this reduction having a deleterious effect on the polymerization.

The object was therefore to find improved reactive or adhesive systems which have a content of organoboron compounds which is as low as possible, and wherein the criteria such as pot life, time to reach the final strength, and strength of the bonding, are likewise optimized.

It has now been found that the required results can be achieved by admixing a peroxide to the monomer component in the reaction system. Peroxides suitable for this purpose are in principle various structural elements, namely both peresters, hydroperoxides, perethers and peranhydrides. This is very surprising since it was absolutely unexpected that such monomer/peroxide mixtures can be manipulated and are stable on storage since it is often difficult even to store the monomer components stably on their own, i.e. to prevent unwanted polymerization.

The invention therefore relates to a two-component reactive system for polymerizing ethylenically unsaturated compounds, comprising as first component monomers capable of the polymerization(=reactive component), and as second component a starter or hardener system composed of organoboron compounds(=initiator component), which are stabilized with suitable oligomers, where these components are mixed for the application, characterized in that an organic peroxide is admixed to the monomers.

The invention further relates to the use of the reactive systems improved according to the invention in the area of joining hard body materials where appropriate together with synthetic material and/or metal in human or animal tissue, in particular also in the area of reactive adhesive or cement systems in the surgical and/or dental sector.

In this case, the peroxide is introduced into, that is to say suspended or dissolved in, the monomer components to be polymerized. The organic peroxides preferably used are those which dissolve in the monomer system.

The peroxide is thus in intimate contact with the reactive end groups of the substances to be polymerized, whereby the complete course of the polymerization is speeded up. The initiation of the polymerization thus takes place on the one hand by the action of the starter on the ethylenically unsaturated compounds, and on the other hand additionally due to the peroxide which is likewise induced to decompose by the starter and acts as polymerization accelerator.

However, a great advantage also derives from the fact that addition of the peroxide to the monomer allows the content of organoboron compound in the initiator component to be reduced, which is important in respect of toxicology.

It is possible in principle to use for this purpose all organic peroxides, that is to say peresters, hydroperoxides, perethers and peranhydrides. However, the selection is also determined by their distribution in the substances to be polymerized, a solution being preferred to suspensions. In addition, the peroxides or reaction catalysts which can be admixed must not be prone to decomposition at room temperatures or below 50° C. The peroxides preferably used have a half-life at 80° C. in the range from hours to days.

Particularly preferred peroxides have proved to be tert-butyl peroxybenzoate or di-tert-butyl peroxide.

The peroxides are admixed in an amount of from 0.005 to 10% by weight, preferably from 0.1 to 5% by weight, based on the monomer components.

The hardener or starter component employed in the reactive systems according to the invention are boron compounds having alkyl and/or aryl radicals, or bicyclic organoboron compounds, which are stabilized or retarded with suitable oligomers. Such a stabilization can preferably take place by the appropriate organic boron compounds being in the form of mixtures with oligomers or of adducts with unsaturated fats or oligomers resulting from a hydroboration reaction. These starter systems are well known to the skilled person and are, for example, described in detail in the documents DE 39 39 164, DE 32 07 263 or DE 32 07 264. This will therefore be dealt with only briefly below.

Thus, a preferred way of stabilizing the organoboron compounds is to prepare physical mixtures of these compounds with oligomers. One possibility for retardation is to mix the organic boron compounds homogeneously with an organic oligomer or polymer which is liquid or solid at room temperature and, where possible, compatible with the body. Suitable oligomeric or polymeric organic components in this case are preferably oligoesters, oligoamides and/or oligoethers which are liquids or spreadable pastes at room temperature.

A particularly preferred starter system consists of oxygen-reactive organoboron compounds in combination with a carrier material which is in the form of an oligoester of lower hydroxy carboxylic acids.

The essential ester-forming constituent of these carrier materials are thus hydroxy carboxylic acids of the preferred C number range from about 2 to 10.

Particularly important hydroxy carboxylic acids are glycolic acid and/or, in particular, lactic acid, which can be used in the form of selected isomers or else as mixture of isomers. Also suitable are the optionally isomeric α- or β-hydroxypropionic acids, α-, β- or γ-hydroxybutyric acids, o-, m- and/or p-hydroxybenzoic acid.

The oligoesters of the said hydroxy carboxylic acids can also have been prepared using monofunctional and/or polyfunctional reactants which result in oligoesters terminated with hydroxyl groups or with carboxyl groups of the lower hydroxy carboxylic acids being present as carriers.

Suitable coreactants are, in particular, monoalcohols and/or monocarboxylic acids, with corresponding compounds having up to 6 C atoms being preferred. However, particularly suitable as carrier material are oligoesters which have been prepared using polyhydric alcohols or else polyfunctional carboxylic acids. Suitable polyhydric alcohols are 2- to 4-functional alcohols, in particular diols or else glycerol. Suitable polyfunctional carboxylic acids are, in particular, dicarboxylic acids having 2 to 10 C atoms.

The formation of the oligoesters is a conventional esterification reaction carried out in a manner known per se in the presence of suitable catalysts.

In both variants, the carrier materials or the oligomers are then mixed with the organoboron compounds, preferably with exclusion of atmospheric oxygen, possibly with gentle heating where appropriate.

Another possibility for a suitable starter system is to prepare alkylboron compounds which are bound to fatty acid and/or fatty alcohol esters or other oligomers.

These alkylboron compounds are preferably the products of the reaction of borane and/or an organoboron compound having at least one B-H linkage with oligomers or polymers which contain carbon double bonds capable of addition, or with esters of olefinically unsaturated fatty acids and/or olefinically unsaturated fatty alcohols. The compounds can be prepared by subjecting the appropriate starting compounds with carbon double bonds capable of addition to hydroboration with diborane or mono- and/or disubstituted boranes.

Possible and particularly preferred matrix materials are esters of unsaturated monocarboxylic acids (unsaturated fatty acids) with polyhydric alcohols. Suitable polyhydric ester-forming reaction components are, in particular, appropriate compounds with a functionality of up to 6, preferably from 2 to 4. Thus, in the preferred embodiment, monocarboxylic acids of the stated C number range are esterified with polyhydric alcohols—in particular with dihydric, trihydric or tetrahydric alcohols, as matrix for the boron-containing substituents.

It may in this connection be preferred for the polyfunctional ester component to have a comparatively small number of carbon atoms, which may be, for example, in the range from 2 to 10, preferably in the range from 2 to 6. Accordingly, particularly suitable polyfunctional alcohols are the lower glycols such as ethylene glycol, 1,2-propylene glycol, 1,3-propylene glycol, the C4 glycols with terminal and/or internal hydroxyl groups and corresponding C5 and C6 compounds. A particularly preferred alcohol is glycerol or polyhydric alcohols of the pentaerythritol type. Conversely, monofunctional fatty alcohols can be esterified with lower polycarboxylic acids, in particular lower di- or tricarboxylic acids.

Generally suitable as boron compounds for the described variants of the starter component are numerous known alkylborons. Typical representatives are, for example, 9-borabicyclo[3.3.1]nonane and its derivatives such as B-methoxy-9-borabicyclo[3.3.1]nonane, diisopinocampheylborane, dicyclohexylborane, thexylborane (2,3-dimethyl-2-butylborane), 3,5-dimethylborinane or else diisoamylborane.

Of these compounds, 9-borabicyclo[3.3.]nonane (9-BBN) is very particularly preferred for practical reasons.

A compilation of the possibilities for preparing suitable boron compounds is to be found in the monograph by Herbert C. Brown, 1975 "Organic Synthesis via Boranes", published by John Wiley & Sons.

The content of organoboron compound in the starter mixture can be chosen according to the invention to be very much lower than is the case in the hardener systems disclosed to date. The content is from 0.5 to 10% by weight, preferably in the range from 1 to 5% by weight, these data being based on the boron compound. This is a significant advantage, especially also in view of the toxicity of many organoboron compounds.

The boron content in the finished adhesive mixture is preferably in the range from 0.005 to 0.2% by weight.

The polymerizable component in the reactive systems according to the invention are mixtures of one or more free-radical polymerizable monomers, polymers to improve cohesion and adjust the viscosity, where appropriate active fillers to improve the mechanical properties and, where appropriate, stabilizers.

Polymerizable monomers which have been investigated besides methyl methacrylate in combination with methacrylic acid (bone cement) are numerous other systems, some of which have achieved practical significance, compare in this connection J. M. Antonucci, Polymer Science and Technology 14, 357 (1981).

However, particularly suitable monomer components for use within the scope of this invention are oligomer components like those described in the documents DE 32 05 504 and 32 29 635. These are binder systems for surgical purposes, which are characterized in that the absorbable (meth)acrylate components they comprise are (meth)acrylic esters which are liquid or solid at room temperature and have (meth)acrylate residues on polyester oligomer chains from hydroxy carboxylic acids. These free-radical reactive components may moreover have one or, preferably, also more than one (meth)acrylic acid residue on the polyester oligo-segment.

Adhesive systems based on such reactive components are distinguished by a large number of outstanding properties. In particular, they result in cured synthetic materials which can be absorbed by the living body.

The polyester oligosegment is in a preferred embodiment formed from monohydroxy monocarboxylic acids which do not exceed a C number of about 20 in the molecule and, in particular, of about 10. Lower hydroxy carboxylic acids having 2 to 6 C atoms may be particularly important in this connection. Particularly suitable hydroxy carboxylic acids for forming this central piece of the (meth)acrylate compounds are glycolic acid, the isomeric lactic acids, the optionally isomeric α- or β-hydroxypropionic acids, α-, β- or γ-hydroxybutyric acids, o-, m- and/or p-hydroxybenzoic acid. It is moreover possible to use either particular isomers of the said acids or else any mixture.

The polyester oligomers are moreover preferably prepared using monofunctional and/or, preferably, polyfunctional reactants. Particularly suitable coreactants are monoalcohols and monocarboxylic acids. Polyfunctional coreactants for preparing the polyester oligomers are polyfunctional alcohols, in particular 2- to 4-hydric alcohols, or corresponding polycarboxylic acids and their functional reactive derivatives. Lower polyfunctional alcohols such as ethylene glycol, propanediol, in particular 1,2-propanediol, glycerol and the like may have particular importance in this connection.

In all the cases described there is formation of modified ester oligomers which can easily be converted in a manner known per se into the (meth)acrylate compounds to be used according to the invention.

In a very particularly preferred embodiment of the invention, the monomer component employed is a product which is preferably composed of ethylene glycol or glycerol, lactic acid and glycolic acid, with particular preference for the product of ethylene glycol and lactic acid with an average degree of polymerization of less than 10.

Further particularly preferred adhesive systems according to the invention are those which are completely composed—that is to say monomer component and oligomers to stabilize the boron compound—of building blocks such as polyethylene glycol and lactic acid or glycolic acid.

The polymers produced from the reactive components may be degradation resistant or degradable in the body. The same applies to any preformed polymers also used. The starter systems in which oligomeric or polymeric carriers are also used may also optionally be designed to be degradation resistant or absorbable in the body and can be combined in an appropriate manner with the complete system.

If systems which are degradable in the body are employed, hydroxy carboxylic acid residues, in particular corresponding residues of glycolic acid and/or lactic acid, are essential building blocks of the molecules both in the ethylenically unsaturated monomer component and in the polymer components which are to be used where appropriate.

In many cases it may be preferable or necessary to add further auxiliaries such as fillers, for example silica flour or the like. Finally, coloring with suitable dyes or pigments may be preferable.

The mixing ratios of the starter system to the reactive component are in the normal range. For example, the starter systems can be used in amounts of about 0.5 to 30% by weight—based on the material to be polymerized. However, it may be mentioned once again in this connection that the content of organoboron compound within the starter system is considerably lower according to the invention than in the prior art.

The two-component reactive systems described herein are used for joining—that is to say for bonding—hard body materials, for example bones, together, but also to exogenous materials such as synthetic material and/or metal, in human or animal tissue. The use as adhesives or cement systems in the surgical and/or dental sector is moreover preferred.

It is furthermore possible for the reactive systems of the type described to be used for in situ production of individually formed moldings, in particular in connection with the bonding of endogenous hard tissue, where appropriate, together with synthetic material and/or metal.

The components of the reactive system, that is to say the monomer components and the hardener or starter components, are, after they have been produced—if necessary with exclusion of air—, preferably each packed sterile, preferably being dispensed into plastic ampoules. The components are mixed to give the system ready for reaction only immediately before use.

The monomer components are stored in ampoules, preferably in materials with a high diffusion coefficient for oxygen, a low density polyethylene being particularly suitable.

On the other hand, the starter component is likewise preferably stored in a plastic material which has a low diffusion coefficient for oxygen, or in a material which is laminated with metal foils.

The individual components are preferably subjected to sterilization by filtration before dispensing into containers. It may furthermore be advantageous to surface-sterilize the closed ampoules with hydrogen peroxide plasma.

The invention also relates to a two-component reactive system as described above, which is characterized in that it is in the form of a kit ready for use consisting of two or more separate components, one component of which comprises the monomers and another component of which comprises the hardener component.

The mixing of the individual components can preferably take place using mixing systems known per se from (medical) technology, such as, for example, systems for mixing bone cements, reactive adhesives or impression compounds.

The mixing is preferably carried out by a two-component syringe. An example which may be mentioned is the dual chamber syringe known to the skilled person, with fitted static mixer. It is also possible with these mixing systems simply to adjust and vary the mixing ratio of the components. This ensures accurate dosage and rapid mixing even with unfavourable monomer/hardener ratios. Also suitable are, for example, mixing systems supplied by MIXPAC Systems AG.

The addition according to the invention of a peroxide to the monomer components results in a system which is easily manipulated and has a low boron content. The reactive system is further distinguished by a convenient pot life, a rapid rate of hardening and an improved final strength.

The adhesives according to the invention are particularly distinguished by reaching 50% of their final strength within less than 20 minutes after mixing the components.

The strength of these adhesive systems can be determined, for example, by bonding iron sheets which have been sandblasted and degreased within the pot life, and measuring the strength in a tensile shear test.

When hard tissue is bonded in medicine, the strength achieved additionally depends greatly on the pretreatment of the bone material and the storage conditions of the joint parts. For use inside the body, strength measurements on degreased, dry bone tissue have little validity. It appears more relevant to bond moist and greasy bones which have not been pretreated, and to measure the strength on the resulting specimens after storage in (blood) Ringer solution. Under these simulated in vivo conditions, conventional methacrylate adhesives and bone cements achieved tensile strengths of about 60 N cm⁻on bone material (cf. in this connection G. Giebel et al., Biomed. Techn. 26, (1981) 170).

The adhesives according to the invention are thus also characterized in that the strength on bone reaches at least 0.3 MPa in the tensile test in blood or (blood) Ringer solution.

The invention also relates to reaction systems as described above, which are characterized in that they are essentially composed of the building blocks polyethylene glycol and lactic acid or glycolic acid. Systems of this type are particularly suitable for constructing a degradable sheet which prevents unwanted adhesion of organs in operations.

It is assumed that a skilled person is able even without further statements to utilize the above description in the widest scope. The preferred embodiments are therefore to be regarded merely as a descriptive and by no means in any way limiting disclosure.

The complete disclosure in all applications and publications mentioned hereinbefore and hereinafter, including DE 19841342.4 filed Sep. 10, 1998 is included in this application by reference.

The following examples are intended to illustrate the invention in detail.

EXAMPLES

I) Oligohydroxycarboxylic Acids with Hydroxyl End Groups

Preparation from Lactide and Ethylene Glycol

L-lactide S and ethylene glycol are introduced into a stainless steel stirring apparatus and phosphoric acid is added. The mixture is heated under nitrogen to 100° C. over the course of 1 h, kept at this temperature for 15 min and then heated further to 130° C. over the course of 30 min. This temperature is maintained for 5 h, and then the product is discharged hot.

The composition and the oligomer properties are to be found in Table 1 (Example 1).

TABLE 1

Oligohydroxycarboxylic acids with hydroxyl end groups from lactide and ethylene glycol

| | Precursors | | | | | |
|---|---|---|---|---|---|---|
| Example | L-lactide S mol | Ethylene glycol mol | Phosphoric acid | Acid value | Calculated molecular weight G/mol | Characteristics |
| 1 | 2 | 1 | 4.2 mg/g | 7 | 350 | clear viscous, pale yellow |

II) Oligohydroxycarboxylic Acids with Polymerizable End Groups a) From Oligohydroxycarboxylic Acids with Terminal Hydroxyl Groups and Methacrylic Acid The oligohydroxycarboxylic acid with hydroxyl end groups from Example 1 and 1.75 equivalent of methacrylic acid per hydroxyl group are introduced into a three-neck flask with stirrer and water trap. At the same time, 2000 ppm of D,L-tocopherol and 0.2 equivalent of methanesulphonic acid are added. The mixture is evacuated to 900 mbar with rapid stirring and passing through of air, and heated to 105° C. After reducing the pressure further to 500 mbar, the water formed in the reaction is removed in the water trap. After a reaction time of 3.5 h, the pressure is lowered to 100 mbar. The reaction is terminated as soon as 85 to 90% of the water expected in the reaction has formed. The reaction product is adjusted to 100° C., and calcium hydroxide is added to neutralize. After addition of Celite, the mixture is stirred at 105° C., 500 mbar with an air throughput of 300 1 for 1 h. The resulting suspension is filtered hot and the resulting filtrate is introduced into a PE bottle.

b) From Oligohydroxycarboxylic Acids with Terminal Hydroxyl Groups and Methacryloyl Chloride The oligohydroxycarboxylic acid with hydroxyl end groups from Example 1 is dissolved in methyl tert-butyl ether in a three-neck flask. Then 2 equivalents per hydroxyl group of anhydrous potassium carbonate are suspended therein, and a solution of 0.9 equivalent per hydroxyl group of methacryloyl chloride in methyl tert-butyl ether is added dropwise over the course of 30 min. The reaction solution is stirred at room temp. for 24 h and left to stand without stirring for 48 h. The colorless precipitate is filtered off and washed twice with methyl tert-butyl ether. The combined organic filtrates are washed with water and dried over magnesium sulphate. The desiccant is filtered off and then washed twice more with methyl tert-butyl ether. After addition of 500 ppm of Ionol (2,6-di-tert-butyl-4-methylphenol), the solvent is slowly removed over the course of 24 h under reduced pressure. The resulting product is stored in a PE bottle.

The composition of the mixtures and the properties of the polymerizable oligomers are listed in Table 2 (Examples 2–3).

TABLE 2

Oligohydroxycarboxylic acids with polymerizable end groups

| Example | Method | Precursor from Example | Yield % | Characteristics |
|---|---|---|---|---|
| 2 | a) | 1 | >90 | homogeneous, low viscosity, yellow |
| 3 | b) | 1 | 80 | homogeneous, low viscosity, pale yellow | c) From Lactide S and Hydroxylated Methacrylic Esters

The methacrylic acid derivative, L-lactide S, magnesium oxide and Ionol are weighed into a reaction flask and, while stirring and introducing air, heated to 100° C. over the course of 30 min. The temperature is maintained at this for 30 min and then raised to 180° C. over the course of 1 h and maintained for 3 h. After cooling to room temperature, the catalyst is filtered off.

The composition and the oligomer properties are shown in Table 3 (Examples 4–7). The methacrylic acid derivatives used were hydroxyethyl methacrylate (A) and glycerol dimethacrylate (B).

TABLE 3

Methacrylic acid derivatives esterified with oligohydroxycarboxylic acids

| | Precursors | | | | |
|---|---|---|---|---|---|
| Example | L-lactide S mol | Methacrylic acid derivative Type/mol | Magnesium oxide | Calculated molecular weight g/mol | Characteristics |
| 4 | 2 | A/1 | 40 mg/g | 418 | clear, viscous |
| 5 | 3 | A/1 | 40 mg/g | 562 | clear, highly viscous |
| 6 | 4 | A/1 | 40 mg/g | 707 | clear, highly viscous |
| 7 | 3 | B/1 | 40 mg/g | 516 | clear, highly viscous |

III Initiator Component 100 g of the oligohydroxycarboxylic acid with hydroxyl end groups from Example 1 are introduced into a round-bottom flask with distillation apparatus and degassed at 75° C. with stirring for 2 h. Then a borane solution is added dropwise over the course of 30 min. After gas evolution ceases, the solvent is distilled off, initially under 10 mbar and for complete removal under 0.1 mbar.

The compositions of the mixtures are listed in Table 4 (Examples 8–11).

TABLE 4

| | Initiator component | | |
|---|---|---|---|
| | Borane solution | | |
| Example | ml | Type | Characteristics |
| 8 | 16.4 | 9-BBN, 0.5M in THF | homogeneous, viscous, colourless |
| 9 | 49.2 | 9-BBN, 0.5M in THF | homogeneous, viscous, colourless |

TABLE 4-continued

| | Initiator component | | |
|---|---|---|---|
| | Borane solution | | |
| Example | ml | Type | Characteristics |
| 10 | 131.2 | 9-BBN, 0.5M in THF | homogeneous, viscous, pale yellow |
| 11 | 25 | BM-9-BBN, 1M in n-hexane | homogeneous, viscous, colourless |

9-BBN = 9-borabicyclo[3.3.1]nonane
BM-9-BBN = B-methoxy-9-borabicyclo[3.3.1]nonane

IV Reactive Component A

The oligohydroxycarboxylic acids with polymerizable end prepared in Example 2 and 3 are adjusted to a content of 5% by dropwise addition of freshly distilled methacrylic acid with stirring. The amounts of peroxide described in Table 5 are then mixed into these monomers. The compositions of the mixtures are listed in Table 5 (Examples 12–16).

TABLE 5

| | Reactive componenet A | | |
|---|---|---|---|
| | Peroxide | | |
| Example | mg | Type | Characteristics |
| 12 | 100 | TBPB | homogeneous, viscous, pale yellow |
| 13 | 1000 | TBPB | homogeneous, viscous, pale yellow |
| 14 | 2000 | TBPB | homogeneous, viscous, pale yellow |
| 15 | 1000 | DTBP | homogeneous, viscous, pale yellow |
| 16 | 2000 | DTBP | homogeneous, viscous, pale yellow |

DTBP = di-tert-butyl peroxide
TBPB = tert-butyl peroxybenzoate

The following attempts to prepare mixtures with peroxide did not result in homogeneous mixtures. (Table 6, Example 17–19)

TABLE 6

Mixing experiments

| Example | Peroxide mg | Peroxide Type | |
|---|---|---|---|
| 17 | 100 | BP | No mixing |
| 18 | 2000 | LP | No mixing |
| 19 | 1000 | TBHP | Mixing problems: $H_2O$ content of the peroxide |

BP = dibenzoyl peroxide
LP = dilauroyl peroxide
TBHP = tert-butyl hydroperoxide

V Reactive Component B

The methacrylic acid derivative esterified with oligohydroxycarboxylic acids as prepared in Example 4 and 5 are converted into the reactive components by dropwise addition of triethylene glycol dimethacrylate (A), glycerol dimethacrylate (B) or the methacrylic acid derivative (C) prepared in Example 7 with stirring, and then mixing in organic peroxy compounds.

The compositions of the mixtures are listed in Table 7 (Examples 20–26).

TABLE 7

Reactive component B

| Example | Precursor from Example | Admixture Type/% by wt. | Peroxide % by wt. | Characteristics |
|---|---|---|---|---|
| 20 | 4 | — | 1% | homogeneous, viscous |
| 21 | 4 | A/10% | — | homogeneous, viscous |
| 22 | 4 | A/10% | 2% | homogeneous, viscous |
| 23 | 5 | A/20% | 2% | homogeneous, viscous |
| 24 | 5 | A/40% | 2% | homogeneous, viscous |
| 25 | 5 | B/20% | 4% | homogeneous, viscous |
| 26 | 5 | C/50% | 4% | homogeneous, viscous |

VI Tensile Shear Tests on Bonded Iron Sheets and Spongiosa Cubes a) The prepared macromers were used to bond iron sheets sandblasted and degreased on one side (in analogy to DIN 53 281/53 283). The samples have pot lives between two and ten seconds and are tested for their shear strength after having been joined for 6 h at room temperature.

b) Spongiosa cubes were bonded in the same way. The samples are tested for their shear strength after an adhesion time of s h at 37° C. in phosphate buffer.

1. Apparatus: Instron type 4502 tester, consisting of testing frame with traverse, two clamps to receive the iron sheets used, and 10 kN sensor. Software: Instron Series IX, program 03, testing rate: 2 mm/min.
2. Specimens:
   a) Steel sheet 25×100×1.5 mm, sandblasted on one side
   b) spongiosa cube 2×2×2 cm, thawed overnight in buffer pH=7.4 at 37° C., storage in horse serum at 37° C. for 5 min before bonding.
3. Sample preparation:
   a) The steel sheets must be degreased before bonding. This takes place by twice treating the parts in dichloromethane in an ultrasonic bath for 15 minutes and then wiping off adherent metal particles with an acetone-impregnated tissue.
4. Bonding:
   a) Using an apparatus, two steel plates are joined together s o that they overlap by 1 cm (bonding area 250 $mm^2$). One steel plate is fixed on the apparatus and, after removing the air from the mixing needle, the adhesive is applied, the second steel plate is placed on top, and the bonding area is loaded with a weight of 5 kg for 5 min. The bonded steel plates are removed from the apparatus and stored at room temperature until measured in the Instron.
   b) The spongiosa cubes removed from the horse serum are dried using a disposable wipe and, after removing air from the mixing needle, adhesive is applied to the spongiosa cube, the second spongiosa cube is put on top, and the two cubes are fixed in a vice for 2 min. The pair of cubes, which is now bonded, is then removed from the apparatus and stored in phosphate buffer at 37° C. until measured.
5. Standards: DIN 53283 testing of metal adhesives, determination of the strength of overlapping bonds.

(Tensile Shear Test)

The composition of the mixtures and the shear strengths achieved are listed in Table 8 (Examples 27–54).

TABLE 8

Shear strengths for the bonding of iron sheets with monomer adhesives based on oligohydroxycarboxylic acids with polymerizable end groups, and methacrylic acid derivatives esterified with oligohydroxycarboxylic acids

| Example | Initiator component Example | Macromer Example | Mixing ratio | Final strength [N $mm^{-2}$] Sheet | Spongiosa |
|---|---|---|---|---|---|
| 27 | 10 | -* | 1:10 | 8.79 | 0.15–0.21 |
| 28 | 10 | 12 | 1:10 | highly exothermic | |
| 29 | 10 | 13 | 1:10 | highly exothermic | |
| 30 | 10 | 14 | 1:10 | highly exothermic | |
| 31 | 10 | 15 | 1:10 | 11.32 | 0.10–0.28 |
| 32 | 10 | 16 | 1:10 | 11.08 | 0.37 |
| 33 | 10 | -* | 1:4 | 3.43 | 0.15 |
| 34 | 8 | -* | 1:10 | 4.41 | |
| 35 | 8 | 13 | 1:10 | 11.58 | 0.19 |
| 36 | 8 | 14 | 1:10 | 10.88 | 0.15 |
| 37 | 8 | 15 | 1:10 | 8.79 | 0.18 |
| 38 | 8 | 16 | 1:10 | 7.88 | 0.15 |
| 39 | 8 | 13 | 1:4 | 11.40 | |
| 40 | 9 | -* | 1:10 | 4.85 | |
| 41 | 9 | 13 | 1:10 | 10.88 | 0.34 |
| 42 | 9 | 14 | 1:10 | 10.75 | 0.37 |
| 43 | 9 | 15 | 1:10 | 7.52 | |
| 44 | 9 | 16 | 1:10 | 8.54 | |
| 45 | 9 | -* | 1:4 | 4.03 | |
| 46 | 11 | 14 | 1:10 | 10.89 | |
| 47 | 10 | 20 | 1:10 | 7.06 | |
| 48 | 10 | 21 | 1:10 | 6.96 | |
| 49 | 10 | 22 | 1:10 | 7.90 | 0.16 |
| 50 | 10 | 23 | 1:10 | 7.79 | |
| 51 | 10 | 24 | 1:10 | 8.48 | |
| 52 | 10 | 21 | 1:4 | 5.33 | |
| 53 | 10 | 25 | 1:10 | 4.98 | 0.26 |
| 54 | 10 | 26 | 1:10 | 5.33 | 0.37 |

*95% of examples 2 or 3 + 5% of methacrylic acid as described on page 23

From the foregoing description, one skilled in the art can easily ascertain the essential characteristics of this invention and, without departing from the spirit and scope thereof, can make various changes and modifications of the invention to adapt it to various usages and conditions.

The preceding examples can be repeated with similar success by substituting the generically or specifically described reactants and/or operating conditions of this invention for those used in the preceding examples.

What is claimed is:

1. Reactive system comprising a first component comprised of ethylenically unsaturated reactive compounds capable of polymerization, and a second component of a hardener system comprised of organoboron compounds which is stabilized with oligomers, wherein the first component and second component are mixed for use of the reactive system and wherein an organic peroxide having a half-life at 80° C. in the range of from hours to days, selected from t-butyl peroxy benzoate or di-tert-butyl peroxide, is dissolved in the ethylenically unsaturated reactive compounds in an amount between 0.005 to 10% by weight, based on the weight of ethylenically unsaturated reactive compounds.

2. Reactive system according to claim 1, characterized in that the ethylenically unsaturated reactive compounds are oligohydroxycarboxylic acid acrylates or methacrylates.

3. Reactive system according to claim 2, characterized in that the oligohydroxycarboxylic acid acrylates or methacrylates have been prepared using monofunctional and/or difunctional alcohols or carboxylic acids or carboxylic anhydrides.

4. Reactive system according to claim 3, characterized in that ethylenically unsaturated reactive compounds are selected from the group consisting of ethylene glycol, glycerol, lactic acid and glycolic acid.

5. Reactive system according to claim 1, characterized in that said organoboron compounds are selected from the group consisting of boron compounds having alkyl and/or aryl radicals and bicyclic organoboron compounds, and are in the form of mixtures with said oligomers or are in the form of adducts with unsaturated fats or said oligomers resulting from a hydroboration reaction.

6. Reactive system according to claim 5, characterized in that said oligomers are oligoesters of lower hydroxy carboxylic acids having 2 to 10 C atoms.

7. Reactive system according to claim 5, characterized in that 9-borabicyclo[3.3.1]nonane is used as said organoboron compound.

8. Reactive system according to claim 5, characterized in that the content of organ boron compound is in the range from 0.5 to 10% by weight, based on the hardener component.

9. Reactive system according to claim 1, which is an adhesive mixture wherein the boron content in said adhesive mixture is in the range from 0.005 to 0.2% by weight.

10. Reactive system according to claim 1, which is an adhesive mixture that reaches 50% of its final adhesive strength in less than 20 minutes.

11. Reactive system according to claim 1, characterized in that the tensile shear strength on bone in blood or blood-Ringer solution in the tensile test reaches at least 0.3 Mpa.

12. A method of using a reactive system according to claim 1 which comprises joining hard body materials, optionally together with a synthetic material, metal or both, in human or animal tissue.

13. A method according to claim 12, wherein the reactive system is used as a reactive adhesive or cement in a surgical or dental procedure.

14. Reactive system according to claim 1, in the form of a kit ready for use consisting of two or more separate components, wherein one separate component comprises said first component and another separate component comprises said second component.

15. Reactive system according to claim 14, comprising the separate components, each within a separate chamber of a dual-chamber syringe with static mixer.

16. Reactive system according to claim 15, wherein the separate components are within plastic ampoules after production.

17. Reactive system according to claim 16, characterized in that the plastic ampoules comprise materials with a high diffusion coefficient for oxygen.

18. Reactive system according to claim 16, characterized in that said second component is stored in a synthetic material which has a low diffusion coefficient for oxygen, or is stored in material which is laminated with metal foils.

19. Reactive system according to claim 14, characterized in that the separate components are produced and separately packed sterile and are combined to give an adhesive mixture ready for use.

20. Reactive system according to claim 1, wherein the first component and second component are reacted to form a polymerized product.

21. Reactive system according to claim 20, characterized in that the polymerized product is suitable for constructing a degradable sheet which prevents unwanted adhesion of organs in operations.

* * * * *